(12) United States Patent
Rotenstreich

(10) Patent No.: US 11,903,879 B2
(45) Date of Patent: Feb. 20, 2024

(54) METHOD FOR DELIVERY OF COMPOSITIONS TO THE EYE

(71) Applicant: TEL HASHOMER MEDICAL RESEARCH INFRASTRUCTURE AND SERVICES LTD., Ramat Gan (IL)

(72) Inventor: Ygal Rotenstreich, Kfar Bilu (IL)

(73) Assignee: Everads Therapy Ltd., Tel Aviv (IL)

( * ) Notice: Subject to any disclaimer, the term of this patent is extended or adjusted under 35 U.S.C. 154(b) by 947 days.

(21) Appl. No.: 16/830,784

(22) Filed: Mar. 26, 2020

(65) Prior Publication Data

US 2020/0222233 A1 Jul. 16, 2020

Related U.S. Application Data

(62) Division of application No. 14/903,350, filed as application No. PCT/IB2014/063624 on Aug. 1, 2014, now abandoned.

(60) Provisional application No. 61/861,575, filed on Aug. 2, 2013.

(51) Int. Cl.
*A61F 9/009* (2006.01)
*A61F 9/00* (2006.01)
*A61F 9/008* (2006.01)

(52) U.S. Cl.
CPC ............ *A61F 9/009* (2013.01); *A61F 9/0008* (2013.01); *A61F 9/0017* (2013.01); *A61F 9/00836* (2013.01); *A61F 9/00825* (2013.01); *A61F 2009/00853* (2013.01); *A61F 2009/00863* (2013.01); *A61F 2009/00865* (2013.01); *A61F 2009/00872* (2013.01)

(58) Field of Classification Search
CPC ...... A61F 9/009; A61F 9/0008; A61F 9/0017; A61F 9/00836; A61F 2009/00853; A61F 2009/00865

See application file for complete search history.

(56) References Cited

FOREIGN PATENT DOCUMENTS

WO WO-2012073180 A1 * 6/2012 ........... A61F 9/0017

* cited by examiner

*Primary Examiner* — Courtney B Fredrickson
(74) *Attorney, Agent, or Firm* — Dekel Patent Ltd.; Dsvid Klein

(57) ABSTRACT

The present invention discloses a device suitable for delivery of a fluid composition to an eye, especially therapeutic compositions, comprising: a hollow needle with a bore having a proximal end and a distal end, said distal end configured to pass into a passage in a sclera of an eye, said bore configured to function as a conduit for a fluid from said proximal end to said distal end, and a solid separator having a distal tip, configured to move inside said bore of said hollow needle allowing said distal tip of said separator to protrude from said distal end of said needle.

17 Claims, 10 Drawing Sheets

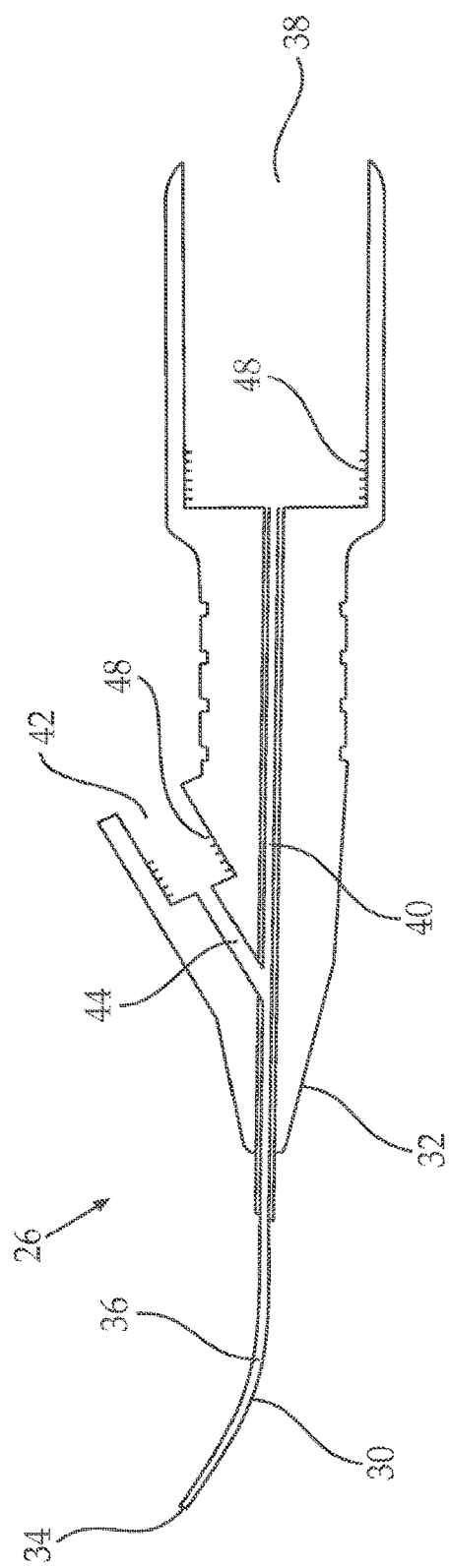
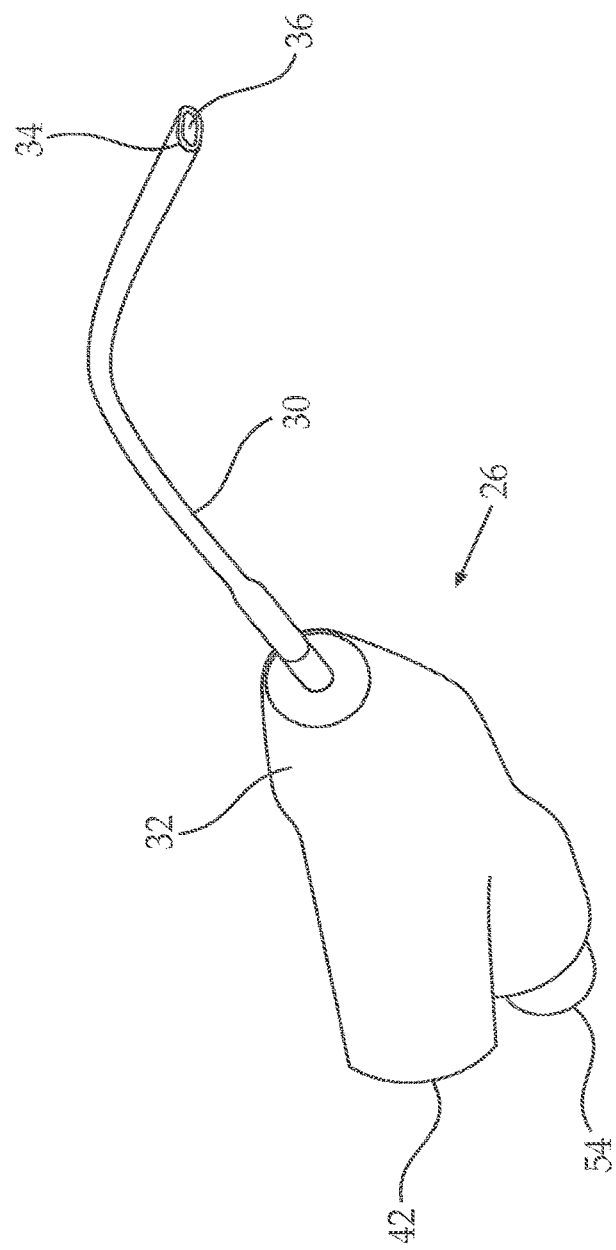
FIGURE 2B
FIGURE 2C

METHOD FOR DELIVERY OF COMPOSITIONS TO THE EYE

RELATED APPLICATION

The present application gains priority from U.S. Provisional Patent Application No. 61/861,575 filed 2 Aug. 2013, which is included by reference as if fully set-forth herein.

The present application is related to the patent application published as US 2013/0253416 by the Inventor, which is included by reference as if fully set-forth herein.

FIELD AND BACKGROUND OF THE INVENTION

The invention, in some embodiments, relates to the field of ophthalmology. The posterior five-sixths of a mammalian eye 10, a portion of which is schematically depicted in cross section in FIG. 1, comprises a number of layers: the outer conjunctiva 12 (typically about 50 micrometers thick), the tough fibrous sclera 14 (typically about 500-600 micrometers thick near the front of the eye), the choroid 16 (typically about 100-200 micrometers thick near the front of the eye), the retinal pigment epithelium (RPE) 18 (typically about 20-25 micrometers thick near the front of the eye) and the sensory retina 20 (typically about 200-300 micrometers thick near the front of the eye). The border between the RPE 18 and the sensory retina 20 is the subretinal space 22. The border between the sclera 14 and the choroid 16 is the suprachoroidal space.

Neuroretinal degenerative diseases such as retinitis pigmentosa and age-related macular degeneration (AMD), which involve death of cells in the RPE layer, are the major causes of blindness in the Western world.

Retinitis pigmentosa is a group of inherited diseases associated with abnormalities of the photoreceptors or the RPE, and characterized by progressive peripheral vision loss and night vision difficulties that can lead to central vision loss.

AMD is a progressive disease which primarily affects the macula, an oval-shaped highly pigmented yellow spot near the center of the retina that includes the fovea which is responsible for central vision. The majority of AMD sufferers have early AMD, associated with minimal visual loss, but which may progress to dry AMD or the more serious wet AMD. In early AMD, the transport of nutrients and waste by the RPE slows down, so that waste accumulates under the retina forming yellowish deposits called drusen. Dry AMD is a slowly progressive condition characterized by the accumulation of drusen under the retina, with some visual loss. With increasing drusen accumulation, the overlying photoreceptors become damaged and atrophy. In wet AMD, new blood vessels grow underneath the retina in a process called choroidal neovascularization. These blood vessels may leak blood or fluid under the retina, causing the retinal surface to become uneven, so that portions of the visual field are distorted. As the condition progresses, blind spots may appear.

It has been suggested that cell-based therapy, where cells, such as progenitor cells or stem cells are transplanted into the subretinal space, may prove efficacious for several currently untreatable conditions involving the RPE, such as retinitis pigmentosa and AMD.

Subretinal injection is commonly used clinically for the delivery of therapeutic compositions to the subretinal space. An efficient delivery method is expected to achieve a uniform distribution of injected composition throughout the subretinal space including to the macula.

Known methods of subretinal delivery include those in which a sharp injection device, e.g., a syringe having a sharpened hollow needle, is used to penetrate the sclera from outside the eye to the subretinal space where the composition is injected. A major drawback of this method is that the composition remains localized in the subretinal space near the injection site and does not reach the macula.

Other methods which are intended to deliver compositions to the macula include inserting a thin flexible catheter from an incision site in the front sclera, through the subretinal space from the incision site until the distal end of the catheter is near the macula to deliver the composition near the macula. Disadvantages of such methods include the risk of severe detachment of the retina from the sclera caused by the catheter, and risk of damaging the retina during the procedure.

In another known method, an incision is made in the frontal part of the sclera and a sharp rigid cannula is inserted into an incision in the eye, across the eye, through the vitreous humor chamber to pierce the sensory retina across the incision site to enter the subretinal space near the macula where the composition is delivered. In addition to the fact that the injected compound remains localized in the subretinal space near the injection site, other drawbacks of this vitrectomy-like surgery include increased chance of cataract development, high ocular pressure and bleeding in the eye. Moreover, the need for repeated injections may require several incisions in the frontal part of the sclera.

The inventor has disclosed advantageous methods and devices for subretinal injection of therapeutic compositions in PCT publication WO 2012/073180, later republished as US 2013/0253416.

SUMMARY OF THE INVENTION

Some embodiments of the invention relate to methods and devices for delivery of compositions, especially therapeutic compositions, to the eye, specifically, to the suprachoroidal space and/or the choroid and/or the subretinal space According to an aspect of some embodiments of the invention there is provided a method for delivery of a fluid composition to the eye of a subject in need thereof, the method comprising:
 a) advancing a distal tip of a solid separator through a passage from outside the eye, through the conjunctiva, followed by through the sclera followed by into the choroid of an eye, thereby creating a separation in the eye; and
 b) injecting an amount of fluid composition into the separation thereby delivering the fluid composition to the eye. In some embodiments, during the advance, the separator does not pass through the sensory retina.

According to an aspect of some embodiments of invention there is also provided a method for delivery of a fluid composition to the eye of a subject in need thereof, the method comprising:
 a) advancing a distal tip of a solid separator through a passage from outside the eye, through the conjunctiva, followed by through the sclera, where the separator is configured to guide light suitable for physically damaging tissue from a proximal end to the distal tip of the separator;

b) subsequent to 'a', projecting light suitable for physically damaging tissue from the distal tip of the separator, thereby creating a separation in the choroid and/or RPE; and c) injecting an amount of fluid composition into the separation thereby delivering the fluid composition to the eye. In some embodiments, the method further comprises: at least once, subsequent to 'b', advancing the distal tip of the separator into the separation. In some such embodiments, subsequent to the advancing the distal tip into the separation, projecting light suitable for physically damaging tissue from the distal tip of the separator, thereby creating a separation in the choroid and/or RPE. In some embodiments, during the advance, the separator does not pass through the sensory retina.

According to an aspect of some embodiments of the invention, there is also provided a device suitable for delivery of a fluid composition to an eye, the device comprising: a hollow needle with a bore having a proximal end and a distal end, the distal end configured to pass into a passage in a sclera of an eye, the bore configured to function as a conduit for a fluid from the proximal end to the distal end of the needle; and a solid separator having a distal tip, configured to move inside the bore of the hollow needle allowing the distal tip of the separator to protrude from the distal end of the needle. In some embodiments, the separator is blunt-tipped. In some embodiments, the separator is devoid of sharp edges.

Unless otherwise defined, all technical and scientific terms used herein have the same meaning as commonly understood by one of ordinary skill in the art to which the invention pertains. In case of conflict, the specification, including definitions, will take precedence.

In addition, the materials, methods, and examples are illustrative only and not intended to be limiting.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetic symptoms of a condition or substantially preventing the appearance of clinical or aesthetic symptoms of a condition.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein, when a numerical value is preceded by the term "about", the term "about" is intended to indicate +/−10%.

The term "pharmaceutically effective amount" denotes that dose of an active ingredient or a composition comprising the active ingredient that will provide the therapeutic effect for which the active ingredient is indicated.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIGS. 2A to 2F are schematic depictions of an embodiment of a device according to the teachings herein;

DESCRIPTION OF SOME EMBODIMENTS OF THE INVENTION

Figure 1:
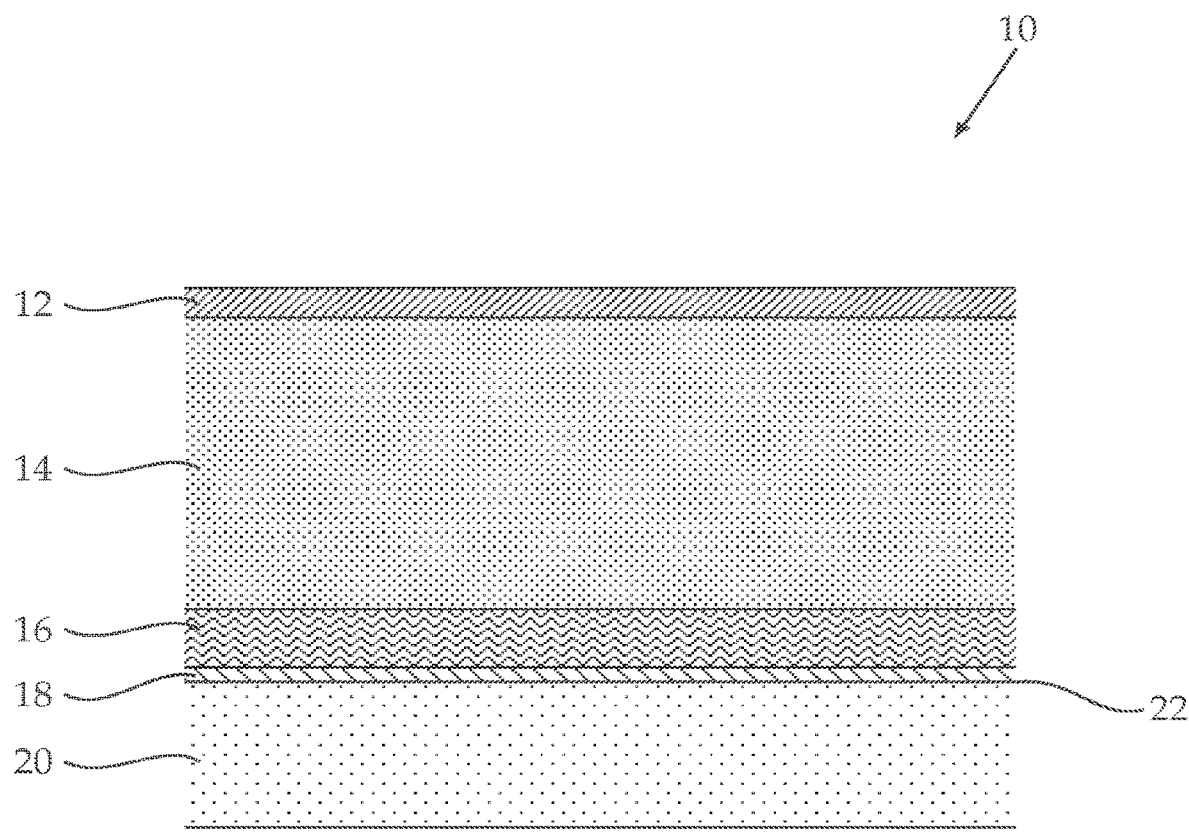
FIG. 1 is a schematic depiction of a cross section of an eye showing various layers.

Some embodiments of the invention relate to methods and devices for delivery of compositions, especially therapeutic compositions, to the eye, specifically, to the suprachoroidal space and/or the choroid and/or the subretinal space.

Before explaining at least one embodiment in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

In US 2013/0253416, the present inventor discloses methods and devices for subretinal injection of fluid compositions, that in some embodiments force an injected fluid composition into the subretinal space 22 of an eye, thereby at least partially separating and detaching the sensory retina 20 from the RPE 18. As reported in US 2013/0253416, despite the detachment of the sensory retina, the intraocular pressure holds the sensory retina in place with the proper shape and, in some embodiments, assists in uniformly distributing the injected fluid composition in the subretinal space including to the macula.

Herein are disclosed methods and devices for injection of fluid compositions to an eye that in some embodiments differ from the disclosed in US 2013/0253416 at least by including the use of a solid separator that is physically inserted from outside the eye into the layers of the eye below the sclera 14 (choroid 16, and in some embodiments RPE 18) but without penetrating through the sensory retina 20. The insertion of the separator causes local physical damage to the layers (the damage herein called a separation). It has been found that in some embodiments such physical insertion of a separator into the eye tissue to create a separation provides at least some advantages in subsequent injection of a fluid composition.

Administration to the Suprachoroidal Space

In some embodiments where the separator is advanced only a short way into the choroid so that the separation is shallow, that is to say close to the sclera-choroid interface, subsequently-injected fluid composition is primarily distributed in the suprachoroidal space, typically uniformly around a substantial portion of the eye, even around substantially all the eye. Without wishing to be held to any one theory, it is currently believed that the separation created by insertion of the separator into the choroid causes some detachment of the choroid from the sclera, and this detachment provides an entry point for subsequently injected composition into the suprachoroidal space.

Administration also to the Choroid

In some embodiments where the separator is advanced further into the choroid so that separation is somewhat deeper into the choroid but without penetrating the RPE, the separator creates a separation which is substantially the volume of choroid occupied by the distal end of the separator. Although not wishing to be held to any one theory, apparently as the separator advances through the choroid, choroid blood vessels and extravascular matrix are pushed aside to make room for the separator. The volume of the choroid occupied by the separator, and possibly also a volume of the choroid extravascular matrix damaged by the advancing separator constitutes the separation into which a fluid composition is subsequently injected.

It has been found that a fluid composition subsequently injected into the separation does not form a bolus, but is typically uniformly distributed into at least a portion of the extravascular compartment of the choroid as well as into the suprachoroidal space. It has been found that the thus-injected fluid composition is uniformly distributed in at least a layer of the entire extravascular compartment of the choroid and is also therapeutically effective.

In some embodiments, the distribution of fluid composition in the extravascular compartment of the choroid is dependent on the depth of penetration of the separator into the choroid. For example, in some embodiments when the separator is advanced into the choroid relatively shallowly, injected fluid composition is distributed in a layer of the choroid extravascular compartment close to the sclera around a large portion or the entire eye (it can be considered that fluid composition is distributed in a stratum of the choroid extravascular compartment around some, most or all of the eye), and does not penetrate more deeply into the choroid. However, in some embodiments when the separator is advanced deeply into the choroid (e.g., almost contacting or contacting the RPE), injected fluid composition is distributed in the entire depth of the choroid extravascular compartment, typically uniformly distributed in the entire depth of the choroid extravascular compartment.

Administration also to the Subretinal Space

In some embodiments where the separator is advanced further through the choroid and into and through the RPE, so as to contact a portion of the sensory retina (and in some embodiments, to slide across the surface of the sensory retina) so that the separation includes part of the RPE, subsequently injected composition is distributed in the suprachoroidal space, in the choroid extravascular compartment, and also in the subretinal space. Without wishing to be held to any one theory, apparently the separation created by penetration through the RPE may causes some detachment of the RPE from the sensory retina and, if sufficiently large, this detachment provides an entry point for subsequently injected composition into the subretinal space.

The thus-injected composition does not form a bolus of composition in the subretinal space localized around the separation. Instead, the sensory retina increasingly detaches from the RPE with the injected composition distributed relatively uniformly in the subretinal space of the eye including to the macula. This relatively uniform distribution is apparently at least partially a result of the force applied to the injected composition by the sclera/choroid on one side and the vitreous fluid/sensory retina on the other.

Damage to RPE

It is important to note that a priori it could be expected that injection of composition when the separation penetrates through the RPE would damage the RPE, e.g., separating the RPE from the choroid or tearing the RPE. Surprisingly, it has been found that typically the structure of the RPE and choroid remains intact and that the RPE and choroid remain attached one to the other, despite injection of the fluid composition.

Separator Contact with the Sensory Retina

It is important to note that a priori, it could be expected that the separator could penetrate into or through the sensory retina when advanced through the RPE. Instead, it has been found that the sensory retina is sufficiently tough that if the separator contacts a surface of the sensory retina under the conditions described herein, the separator slides across the sensory retina surface without causing substantial damage, if at all, thereto.

Damage to Choroid Blood Vessels

It is important to note, that it has been found that in some embodiments, advancing the separator into and through the choroid does not damage the choroid blood vessels or cause bleeding, the choroid blood vessels seemingly moving away from the advancing separator distal tip. Although not wishing to be held to any one theory, it is currently believed that this is a result of the separator being blunt tipped and/or devoid of sharp edges. Since the choroid blood vessels are not damaged, administered composition is more likely to stay in the choroid and not be transported away by the circulatory system.

Method for Delivery of a Fluid Composition to an Eye

Thus, according to an aspect of some embodiments of the teachings herein, there is provided a method for delivery of a fluid composition to the eye of a subject in need thereof, the method comprising:
  a) advancing a distal tip of a solid separator through a passage from outside the eye, through the conjunctiva, followed by through the sclera followed by into the choroid of an eye, thereby creating a separation in the eye; and
  b) injecting an amount of fluid composition into the separation thereby delivering the fluid composition to the eye.

In some embodiments, during the advance, the separator does not pass through the sensory retina. In some embodiments, during the advance the separator does not penetrate into the sensory retina. In some embodiments, during the advance the separator contacts a surface of the sensory retina from the RPE side, in some embodiments, the separator sliding across the surface of the sensory retina.

In some embodiments, choroid blood vessels are not damaged during the advance of the distal tip of the separator, so no bleeding occurs as a result of the advancing.

In some embodiments, the subject is a living human. In some embodiments, the subject is a living non-human animal undergoing veterinary treatment. In some embodiments, the subject is a living non-human animal undergoing an industrial process, e.g., for producing a product useful in science, research or technology. In some embodiments, the subject is a non-living animal. In some embodiments, the subject is the eye of a non-living animal.

In such embodiments, the term "separation" that is created in the eye by the advance of the distal tip of the solid separator into the choroid and/or RPE includes physical damage caused by the separator to the choroid and/or RPE, for example, a gap, void, tear or disruption in the choroid extravascular matrix and/or RPE. In some instances, especially in the priority document, the term "separation formed" is used as a synonym for "separation created".

The various (preferred) attributes, dimensions and properties of some embodiments of the separator are as described herein with reference to the device according to the teachings herein and are not repeated here for the sake of brevity.

Location of Separator During Injection

In some embodiments, during the injecting the separator is at least partially located in the created separation.

In some embodiments, prior to the injecting, the separator is at least partially withdrawn from the separation.

In some embodiments, prior to the injecting, the separator is completely withdrawn from the separation.

Injection to the Suprachoroidal Space, Choroid and Subretinal Space

In some embodiments, during the advance, the distal tip of the separator passes into the choroid of the eye and does not substantially contact the RPE. In some such embodiments, the separation is located exclusively in the choroid of the eye, and the fluid composition is injected into the suprachoroidal space and/or choroid of the eye. In some such embodiments, the fluid composition is injected substantially exclusively into the suprachoroidal space of the eye.

In some embodiments, during the advance, the distal tip of the solid separator contacts and damages a portion of the RPE, so that a portion of the separation is in the RPE. In some such embodiments, the fluid composition is injected into the subretinal space of the eye. In some such embodiments, the fluid composition is injected concurrently into the subretinal space, choroid and suprachoroidal space of the eye.

Advancing the Separator

In some embodiments, during the advance, the separator is at an angle not greater (i.e., is not more obtuse) than 45° and even not greater than 30° from parallel to the layers of the eye, e.g., to the outer surface of the eye, to the subretinal space of the eye.

Hollow Needle

In some embodiments, the passage at least partially comprises the bore of a hollow needle (in some embodiments, a blunt-tipped needle) for example the portion of the passage passing through the sclera. The various (preferred) attributes, dimensions and properties of some embodiments of the hollow needle are as described hereinbelow with reference to the device according to the teachings herein and are not repeated here for the sake of brevity.

In some embodiments, during the advance, the distal end of the needle is maintained at an angle not greater (i.e., is not more obtuse) than 45° and even not greater than 30° from parallel to the layers of the eye, e.g., to the outer surface of the eye, to the subretinal space of the eye.

In some embodiments, during the advance of the separator, a distal end of the needle is located in a channel through the sclera. In some such embodiments, the channel is a converging channel, so that the dimensions of a proximal end of the channel near the outer portion of the sclera are greater than the dimensions of a distal end of the channel near the inner portion of the sclera. In some such embodiments, the dimensions of a distal tip of the needle are larger than the dimensions of a portion of the channel in the sclera. In some such embodiments, the dimensions of a distal tip of the needle are larger than the dimensions of the distal end of the channel. In some such embodiments, during the advancing the separator, the tip of the needle is pressed into the channel. In some such embodiments, especially when the needle is a blunt-tip needle, such pressing allows the needle to act as a tamponade. In some such embodiments, during the injecting of the fluid compositions, the tip of the needle is pressed into the channel. In some such embodiments, especially when the needle is a blunt-tip needle, such pressing allows the needle to act as a tamponade. In some such embodiments, especially when the needle is a blunt-tip needle, such pressing creates a seal between the needle tip and the channel walls that substantially prevents retrograde passage of the fluid composition in the channel past the needle, thereby assisting in forcing the fluid composition into the separation created by the separator and in subsequent distribution of the injected composition in the eye.

Making a Channel

In some embodiments, prior to the passing of the separator through the passage, the method comprises making a channel through the sclera to the choroid, in some embodiments substantially as described in US 2013/0253416 by the Inventor. The channel may be made using tools such as diamond knives (e.g., AccuSharp® knives by Accutome Inc., Malvern, PA, USA) known in the art of ophthalmic surgery.

In some embodiments, the entire channel from the scleral surface to the choroid is oriented at an angle not greater (i.e., is not more obtuse) than 45° and even not greater than 30° from parallel to the layers of the eye, e.g., to the outer surface of the eye or the subretinal space of the eye.

In some embodiments, the channel is substantially a slit. In some such embodiments, the channel is made by advancing a flat blade into the sclera.

As noted above, in some embodiments, the channel is a converging channel, so that the dimensions of a proximal end of the channel near the outer portion of the sclera are greater than the dimensions of a distal end of the channel near the inner portion of the sclera.

In some such embodiments, the channel is made by advancing a convergent (pointed) blade into the sclera.

In some embodiments, the first portion of the channel penetrates from the scleral surface substantially perpendicular to the scleral surface, while a second portion passes from the end of the first portion to the choroid at an angle not greater (i.e., is not more obtuse) than 45° and even not greater than 30° from parallel to the layers of the eye, e.g., to the subretinal space of the eye or to the scleral surface. Typically, the first portion is to a depth of between 33% and 60% of the scleral thickness. It is believed that in some embodiments such a two-part channel heals more easily.

Typically, prior to making the channel through the sclera, a portion of the outer conjunctiva is cut and folded as a flap to expose the surface of the sclera. When the procedure is complete, the flap is placed over the exposed surface of the sclera, helping in healing the sclera.

Typically it is desired that the channel reach the choroid but that the tool used to make the channel not penetrate to the choroid to damage the choroid and the blood vessels thereof. If the tool used penetrates too deeply to the choroid, typically blood is observed emerging from the channel. In some embodiments, the presence of blood is used as an indication that the channel is deep enough. In some embodiments, the performing person (e.g., surgeon), makes the channel based on judgment to avoid damaging the choroid blood vessels. In such embodiments, if the channel does not pass through the sclera to reach the choroid, the separator is not able to penetrate through the remaining sclera, indicating that the channel must be extended. In some embodiments, the thickness of the sclera at the location where the channel is to be made is measured (in the usual way), and then the extent the tool used to make the channel needs to be advanced is calculated based on the measured thickness and desired entry angle. In some such embodiments, the tool used to make the channel is marked or provided with a stop, assisting in ensuring that the tool does not penetrate too deeply into the eye to damage the choroid blood vessels.

In some embodiments, a guide is used to assist in making the channel through the sclera by helping the one making the channel choose the correct angle and depth. For example, in some embodiments the guide is a physical component that rests on the surface of the eye and has a known height from the scleral surface. The one making the channel rests the tool on the guide and accounts for the scleral thickness, the desired channel angle and the height of the guide using simple geometry. In some embodiments, different portions of the guide have different heights, giving the one making the channel the option to choose a desired height. In some embodiments, the guide has one or more surfaces beveled at a useful angle or angles, e.g., some angle not greater than 45°. The one making the channel rests the tool on a surface of the guide, ensuring the desired angle to properly penetrate through the sclera. In some embodiments, such a guide is ring shaped and is also suitable for immobilizing the eye, see below. In some embodiments, such a guide is a ring shape around which circumference are one or more beveled surfaces sloping at one or more angles, and at one or more heights.

Injecting

In some embodiments, the injecting of the fluid composition is through the passage, for example, through the bore of the hollow needle.

Composition

The amount of fluid composition injected is any suitable amount, and is typically determined by a medical professional depending on various clinical parameters. In some embodiments where the subject is a human, the amount of fluid composition injected is not more than about 70 microliters and even not more than about 50 microliters.

In some embodiments, the fluid composition is a liquid.

In some embodiments, the fluid composition is a therapeutic composition. In some such embodiments, the composition comprises at least one active pharmaceutical ingredient. In some such embodiments, the composition comprises viable cells, e.g., stem cells.

Monitoring

The progress of the method may be monitored in any suitable way, for example using imaging methods such as imaging methods known in the art. In some embodiments, monitoring is at least partially performed by capturing images in the vicinity of the distal tip of the separator, in the vicinity of the separation and/or (when present) in the vicinity of the distal tip of the needle. In some embodiments, the images are captured with the help of an optical fiber which passes through the passage. In some embodiments, the optical fiber is a dedicated optical fiber. Additionally or alternatively, in some embodiments, the separator is configured to function as an optical fiber.

Pre and Post Operation

Generally, prior to implementing the method, the area of the eye is prepared for surgery in the appropriate way, for example with the use of antiseptics such as povidone-iodine.

In some embodiments local or general anesthesia is optionally administered. Local anesthetics may comprise an aminoamide (such as articaine, bupivacaine, dubicaine, etidocaine, levobupivacaine, lidocaine, mepivacaine, prilocaine, ropivacaine or trimecaine) or an aminoester (such as benzocaine, chloroprocaine, cocaine, cyclomethylcaine, dimethocaine, piperocaine, propoxycaine, novocaine, proparacaine, or teteracaine), or a combination local anesthetic such as lidocaine/prilocaine.

In some embodiments of the method, an eyelid speculum is used to retain the eyelid of the subject in an open position for at least some of the procedure.

In some embodiments of the method, the eye is immobilized, see for example US 2013/0253416 by the Inventor. Immobilization of the eye may be achieved using any suitable method and any suitable device or devices, for example as known in the art of ophthalmology. For example, in some embodiments, an appropriately shaped ring pressed against the eye by physical pressure or application of a vacuum as known in the art of ophthalmology. As noted above, in some embodiments an immobilizing device can also be configured to help guide the making of the channel through the sclera.

Creating a Separation with the Use of Light

In some embodiments of the method described above, a separation is created in the choroid and optionally in the RPE by damage caused by the physical presence of the separator that advances through the layers of the eye. In some embodiments, some or all of a separation is created with light suitable for physically damaging tissue (e.g., by ablation, for example light generated by a laser microkeratome as known in the art of LASIK).

Accordingly, in some embodiments, the method further comprises: c) at least once during 'a', projecting light suitable for physically damaging tissue from the distal tip of the separator, thereby creating at least a portion of the separation. In some such embodiments, bleeding from choroid blood vessels damaged as a result of the projected light is prevented by the cauterization effect of the light.

Such embodiments may be implemented in any suitable way. In some preferred embodiments, the separator is configured to function as a light guide for guiding light suitable for physically damaging tissue from a proximal end of the light guide to the distal tip. When a suitable light source. e.g., laser microkeratome is activated, the produced light is guided through the separator and projected from the distal tip of the separator, physically damaging tissue (e.g., by ablation), thereby creating a portion of the separation.

In some embodiments, substantially all of the separation is created using light suitable for physically damaging tissue. Specifically, the distal tip of the solid separator is advanced through a passage through the sclera (e.g., of a hollow needle) to face the choroid. A suitable light source. e.g., a laser microkeratome is activated, the produced light is guided through the separator and projected from the distal tip of the separator, physically damaging tissue (e.g., by ablation), thereby creating a portion of the separation. The light is projected one or more times from a given position of the separator. If the thus-created separation is sufficient, the amount of fluid composition is injected into the separation. If required, the distal tip is advanced into (and in some embodiments, not beyond) the thus-created separation. If desired, the light is again projected one or more times and, optionally the distal tip again advanced, until a desired separation is created in the choroid and optionally the RPE.

Thus, according to an aspect of some embodiments according to the teaching herein there is also provided a method for delivery of a fluid composition to the eye of a subject in need thereof, the method comprising:

a) advancing a distal tip of a solid separator through a passage from outside the eye, through the conjunctiva, followed by through the sclera, where the separator is configured to guide light suitable for physically damaging tissue from a proximal end to the distal tip of the separator;

b) subsequent to 'a', projecting light suitable for physically damaging tissue from the distal tip of the separator, thereby creating a separation in the choroid and/or RPE; and c) injecting an amount of fluid composition into the separation thereby delivering the fluid composition to the eye. In some such embodiments, bleeding from choroid blood vessels damaged as a result of the projected light is prevented by the cauterization effect of the light.

In some embodiments, the method further comprises: at least once, subsequent to 'b', advancing the distal tip of the separator into the separation. In some such embodiments, subsequent to the advancing the distal tip into the separation, projecting light suitable for physically damaging tissue from the distal tip of the separator, thereby creating a separation in the choroid and/or RPE.

In such embodiments, the term "separation" that is created in the eye by the projecting of the light into the choroid and/or RPE includes physical damage caused by the projected light to the choroid and/or RPE, for example, a gap, void, tear or disruption in the choroid extravascular matrix and/or RPE. In some instances, especially in the priority document, the term "separation formed" is used as a synonym for "separation created".

Additional features, options and embodiments of the method are substantially the same, mutatis mutandi, as described above for the method creating a separation by advancing the separator so are not repeated here for brevity. A person having ordinary skill in the art upon perusing the specification, is able to understand which such features, options and embodiments are relevant, and what changes are needed, if any, to implement such features, options and embodiments.

Device for Delivery of a Fluid Composition to an Eye

The methods for delivery of compositions to the eye described herein may be implemented using any suitable device or collection of devices. That said, in some embodiments the methods are preferably implemented using a device suitable for delivery of a fluid composition to an eye according to the teachings herein.

According to an aspect of some embodiments of the teachings herein, there is provided a device suitable for delivery of a fluid composition to an eye, comprising:

a hollow needle with a bore having a proximal end and a distal end, the distal end of the hollow needle configured to pass into a passage in a sclera of a (human) eye, the bore of the hollow needle configured to function as a conduit for a fluid from the proximal end of the hollow needle to the distal end of the hollow needle; and a solid separator having a distal tip, configured to move inside the bore of the hollow needle allowing the distal tip of the separator to protrude from the distal end of the hollow needle.

The device is configured to allow the separator to protrude from the distal end of the needle to an extent suitable for implementing an embodiment of the teachings herein. In some embodiments, the device is configured to allow the separator to protrude from the distal end of the needle by not less than 0.3 mm, not less than 0.5 mm, not less than 0.8 mm and even by not less than 1 mm.

In some embodiments, the device is configured to limit the extent of protrusion of the separator from the distal end of the needle, for example, to prevent damage to the separator or to an eye if the separator protrudes too far. In some such embodiments, the device is configured to allow the separator to protrude from the distal end of the needle by not more than 10 mm, not more than 5 mm, not more than 4 mm and even not more than 3 mm.

Hollow Needle

The needle is made of any suitable material or combination of materials, as known in the art of hollow surgical needles. In some embodiments, the needle is made of a metal, for example titanium or stainless steel.

The needle has any suitable shape. For example, in some embodiments, the needle is straight. That said, in some embodiments it has been found that it is easier for an operator to control the depth and angle of the device when the needle is not straight. Accordingly, in some embodiments, the needle is curved along a length thereof. In some embodiments, the needle is bent along a length thereof.

In some embodiments, the distal end of the needle is blunt, that is to say, is not sharp. As described herein, a blunt-ended needle may be pushed against a portion of a tapering passage in a sclera that has a cross-sectional area smaller than of the needle without penetrating or damaging the sclera, thereby forming a seal that allows subsequent injection of a fluid composition at relatively high pressure.

The needle may have any suitable cross-sectional shape and size. Typically, the needle should be as small as possible to reduce the size of the wound in the sclera and in some embodiments, to form an effective seal when pressed into a converging channel in the sclera as described above, but should be sufficiently large for convenient use to be robust, for accommodating the separator inside the bore and for delivering the required amount of fluid composition with sufficiently low resistance.

In some embodiments, the needle has a circular cross section. In some such embodiments, the needle has an outer diameter of not more than 300 micron, not more than 250 micron and in some embodiments not more than 200 micron.

In some embodiments, the needle has a non-circular cross section having an outer height dimension smaller than an outer width dimension. In some embodiments, such a shape is preferred as the smaller height dimension prevents damage to the sclera while the larger width dimension reduces the resistance to fluid flow through the bore of the needle, especially when the separator is disposed therein. In some such embodiments, the non-circular cross section is selected from the group consisting of a flattened circle, an oval, and a rounded-vertice rectangle. In some such embodiments, the needle has an outer height dimension of not more than 300 micrometer, not more than 250 micrometer, and even not more than 200 micrometer. In some embodiments, the needle has an outer width dimension of not more than 1000 micrometer, and even not more than 800 micrometer.

The bore of the needle is of any suitable size and shape, and is related to the outer dimensions of the needle and the wall thickness required to provide sufficient mechanical strength. In some embodiments, typically when the needle has a circular cross section, at a distal tip of the needle the bore has a circular cross section. In some embodiments, typically when the needle has a non-circular cross section, at a distal tip of the needle the bore has a has a non-circular cross section having an inner height dimension smaller than an inner width dimension, for example has a shape selected from the group consisting of flattened circle, oval, and rounded-vertice rectangle.

In some preferred embodiments, the bore is of a size allowing flow of fluid composition therethrough when the separator is disposed therein.

Separator

As noted above, in some embodiments a device according to the teachings herein includes a solid separator having a distal tip, configured to move inside the bore of the hollow needle allowing the distal tip of the separator to protrude from the distal end of the hollow needle. As used herein, the term "solid separator" means that the separator has a state of matter that is not gas or liquid, and includes for example, solid objects that are hollow.

In some embodiments, the separator is elongated (e.g., a wire or like a wire).

In some embodiments, the separator is laterally flexible, that is to say, bendable along the length, allowing bending with the bore of the needle, and across the outer surface of the sensory retina without penetrating therethrough.

In some embodiments, the separator is longitudinally non-compressible, i.e., axially-rigid, allowing accurate transmittal of an extent of movement of the separator from the proximal end inside the bore of the needle to an extent of movement of the distal tip of the separator.

In some embodiments, the separator is blunt tipped and/or devoid of sharp edges. It is believed that a blunt tip helps prevent damage to choroid blood vessels when the separator passes through a choroid of an eye and/or to help prevent damage to the outer surface of the sensory retina if the separator slides there across.

Cross Sectional Size of Separator

The separator has any suitable cross sectional size.

In some embodiments, the separator has a cross-sectional area not more than 75%, in some embodiments not more than 50% and in some embodiments not more than 40% of the cross-sectional area of the bore of the needle, allowing the relatively easy flow of fluid composition through the bore while the separator resides therein.

In some embodiments, the separator has a circular cross section. In some such embodiments, the diameter of the separator is not less than 20 micrometer (cross sectional area 1257 micrometer$^2$), is not less than 30 micrometer (cross sectional area 2800 micrometer$^2$), not less than 40 micrometer (cross sectional area 5000 micrometer) and even not less than 50 micrometer (cross sectional area 7900 micrometer$^2$). In some such embodiments the diameter of the separator is not greater than 300 micrometer (cross sectional area 283000 micrometer$^2$), not greater than 250 micrometer (cross sectional area 196000 micrometer) and even not greater than 200 micrometer (cross sectional area 126000 micrometer$^2$). In some such embodiments, the diameter of the separator is not less than 50 micrometer (and even not less than 75 micrometer) and not more than 200 micrometer (an even not more than 150 micrometer).

In some embodiments, the separator has a non-circular cross section. In such embodiments, the preferred dimensions are those having cross sectional area equivalent to the discussed immediately hereinabove for round cross-section separator.

In some embodiments, the separator is substantially thinner (diameter for circular cross section, height dimension for non-circular cross section) than the choroid that is being penetrated, for example has a diameter of up to 50% of the choroid thickness, e.g. for a 100 micrometer thick choroid, a 50 micrometer or less diameter round separator.

In some embodiments, the separator is only somewhat thinner than the choroid that is being penetrated, for example has a diameter between 50% and 90% of the choroid thickness, e.g. for a 100 micrometer thick choroid, a 50 to 90 micrometer diameter round separator.

In some embodiments, the separator is about the same or somewhat thicker than the choroid that is being penetrated, for example has a diameter between 90% and 150% of the choroid thickness, e.g. for a 100 micrometer choroid, a 90 to 150 micrometer diameter round separator. In some instances when such a thick separator is used, during the advancing the sclera is lifted outwards, the sensory retina is pushed inwards, and in some instances, the RPE damaged by contact with the separator. Accordingly, such separators are typically used when it is desired to administer a fluid composition concurrently to the suprachoroidal space, the choroid and the subretinal space.

In some embodiments, the thickness of the choroid in the area where the separator is to be advanced in the eye is measured, allowing the selection of a suitably-dimensioned separator having a desired thickness relative to the choroid thickness.

That said, the inventor has found that a 80-150 micrometer diameter circular cross section separator is generally useful for treating human eyes in most cases.

Separator Material

The separator can be made of any suitable material or combinations of materials. In some embodiments, the separator comprises a material selected from the group consisting of a metal, a plastic and a glass, In some embodiments, the separator consists of a material selected from the group consisting of a metal, plastic and glass, In some embodiments, the separator comprises (and even consists of) a metal, for example a metal selected from the group consisting of stainless steel and titanium. In some embodiments, the separator comprises a metal and is substantially a wire.

In some embodiments, the separator comprises (and even consists of) a glass, especially a glass fiber.

In some embodiments, the separator comprises (and even consists of) a plastic especially a plastic fiber, for example a plastic selected from the group consisting of PEEK, PMMA, polystyrene and polyperfluorobutenylvinylether, Separator as a Light Guide In some embodiments, especially when the separator comprises or consists of glass and/or plastic, the separator is configured to guide light from the proximal end of the separator to the distal tip and/or from the distal tip to the proximal end, e.g., constitutes an optical fiber. In some such embodiments, the separator comprises cladding configured to assist the transmission of light for example as known in the art of optical fibers, e.g., PMMA with fluorinated polymer cladding.

Some such embodiments are configured for collecting light from the distal tip of the separator, e.g., light having wavelengths in the infrared and/or UV/visible portions of the spectrum. Some such embodiments allow the separator to be used as an imaging fiber optic to view and monitor an area inside the eye during use of the device. In some such embodiments, the device further comprises an imaging component (e.g., a camera and associated display screen suitable for producing an image from light gathered by an optical fiber), where the proximal end of the separator is functionally associated with the imaging component, allowing resolution of an image from light gathered through the distal tip of the separator.

Additionally or alternatively, some such embodiments are configured for guiding light from a proximal end to the distal tip of the separator. In some such embodiments, the separator is configured to guide light suitable for physically damaging tissue (e.g., ablation or other) from a proximal end to the distal tip of the separator. Such light includes, for example, light generated by a laser microkeratome (as known in the art of LASIK). In some such embodiments, the separator is configured to guide light suitable for ablating tissue. In some such embodiments, the separator is configured to guide light generated by a laser microkeratome from a proximal end to the distal end of the separator. In some such embodiments, the device further comprises a source of light suitable for physically damaging tissue (e.g., a laser microkeratome), where the proximal end of the separator is functionally associated with the source of light, allowing projection of light from the distal tip of the separator, allowing tissue (e.g., choroid or RPE) to be physically damaged using light in addition to or instead of physically damaged using the end of the separator.

In some embodiments, a separator is configured to collect light from the distal tip of the separator (e.g., for imaging). In some embodiments, a separator is configured for guiding light from a proximal end to the distal tip of the separator (e.g., for ablation). In some embodiments, a separator is configured to both collect light from the distal tip of the separator (e.g., for imaging), and for guiding light from a proximal end to the distal tip of the separator (e.g., for ablation).

Moving the Separator

As noted above, in some embodiments the separator of the device is configured to move inside the bore of the hollow needle allowing the distal tip of the separator to be moved to protrude from the distal end of the needle.

In some embodiments, the device is configured so that the separator is movable between at least two states: a state wherein the separator does not protrude from the bore of the needle and a state wherein the separator protrudes from the distal end of the needle. In some such embodiments, the configuration is sealed against liquid leakage therethrough, so that if a liquid composition is injected through the needle when the separator is located in the bore of the needle (including when protruding from a distal end thereof), there is no substantial leakage of composition from the device and the fluid exits the device substantially exclusively from the distal end of the needle.

In some such embodiments, the device is further configured for controllably moving the separator between the two states. By controllably is meant that the extent and rate of protrusion of the separator from the distal end of the needle can be controlled by an operator in a repeatable and accurate manner, in some embodiments to an accuracy of better than +0.3 mm, better than +0.2 mm and even better than +0.1 mm.

In some embodiments, the device is configured for controllably moving the separator to protrude from the distal end of the needle by not less than 0.3 mm, note less than 0.5 mm, not less than 0.8 mm and even not less than 1 mm.

In some embodiments, the device is configured for controllably moving the separator to protrude from the distal end of the needle by not more than 10 mm, not more than 5 mm, not more than 4 mm and even not more than 3 mm.

In some such embodiments, the configuration for controllably moving the separator comprises a screw and thread configured so that rotation of a screw component in a first direction controllably advances the separator through the bore of the needle.

Optical Fiber

In some embodiments, the device further comprises an optical fiber different from the separator having a distal end inside the bore of the hollow needle so that a distal tip of the optical fiber is positioned to gather light from outside the hollow needle. In some such embodiments, the device further comprises an imaging component (e.g., a camera and associated display screen suitable for producing an image from light gathered by an optical fiber), where the proximal end of the optical fiber is functionally associated with the imaging component, allowing resolution of an image from light gathered through the distal tip of the optical fiber.

Fluid Composition Injector

As noted above, embodiments of a device according to the teachings herein are suitable for the delivering of a fluid composition to an eye.

In some embodiments, a device according to the teachings herein further comprises an injection port configured to engage a fluid injector when the distal end of the tube is in a passage in a sclera; and the device is configured to direct a fluid that is injected by a fluid injector engaged with the injection port through the bore of the needle and out through the distal end of the needle.

In some embodiments, the device is configured to direct the fluid through the bore and out through the distal end of the needle while the separator is inside the bore, and in some embodiments, when the separator is inside the bore and protruding from the distal end of the needle.

In some embodiments, the device is configured so that substantially all fluid injected by the fluid injector is directed through the bore of the needle and out through the distal end without substantial leakage.

In some embodiments, the injector port is configured to engage a syringe as a fluid injector.

In some embodiments, the device further comprises a composition chamber suitable for containing a composition for administration to an eye, the composition chamber functionally associable with the injection port. In some embodiments, the composition chamber is a portion of a syringe.

In some embodiments, the composition chamber is filled with fluid composition (for example a therapeutic composition for the treatment of an eye disorder) just prior to use, for example by medical personnel participating in a treatment that makes use of the device.

In some embodiments, the composition chamber is sized to contain a desired amount of the therapeutic composition to be dispensed, for example, in some embodiments between about 10 and about 100 microliters, in some embodiments between about 15 and about 75 microliters, and in some embodiments between about 25 and about 50 microliters.

In some embodiments, the device further comprises a therapeutic composition contained in the composition chamber (e.g., is provided pre-charged), for example a therapeutic composition for the treatment of an eye disorder. In some such embodiments, the composition chamber is filled with a required dose of a therapeutic composition.

Embodiment of a Device

A device 24 according to an embodiment of the teachings herein suitable for implementing embodiments of the methods according to the teachings herein is schematically depicted in FIGS. 2A, 2B, 2C, 2D, 2E and 2F. Device 24 comprises three physically separable assemblies: a body assembly 26 (FIGS. 2A, 2B, 2C, 2D and 2F), a separator assembly 28 (FIGS. 2A, 2C, 2D and 2F) and an injector assembly 29 (see FIGS. 2E and 2F).

Figure 2A:
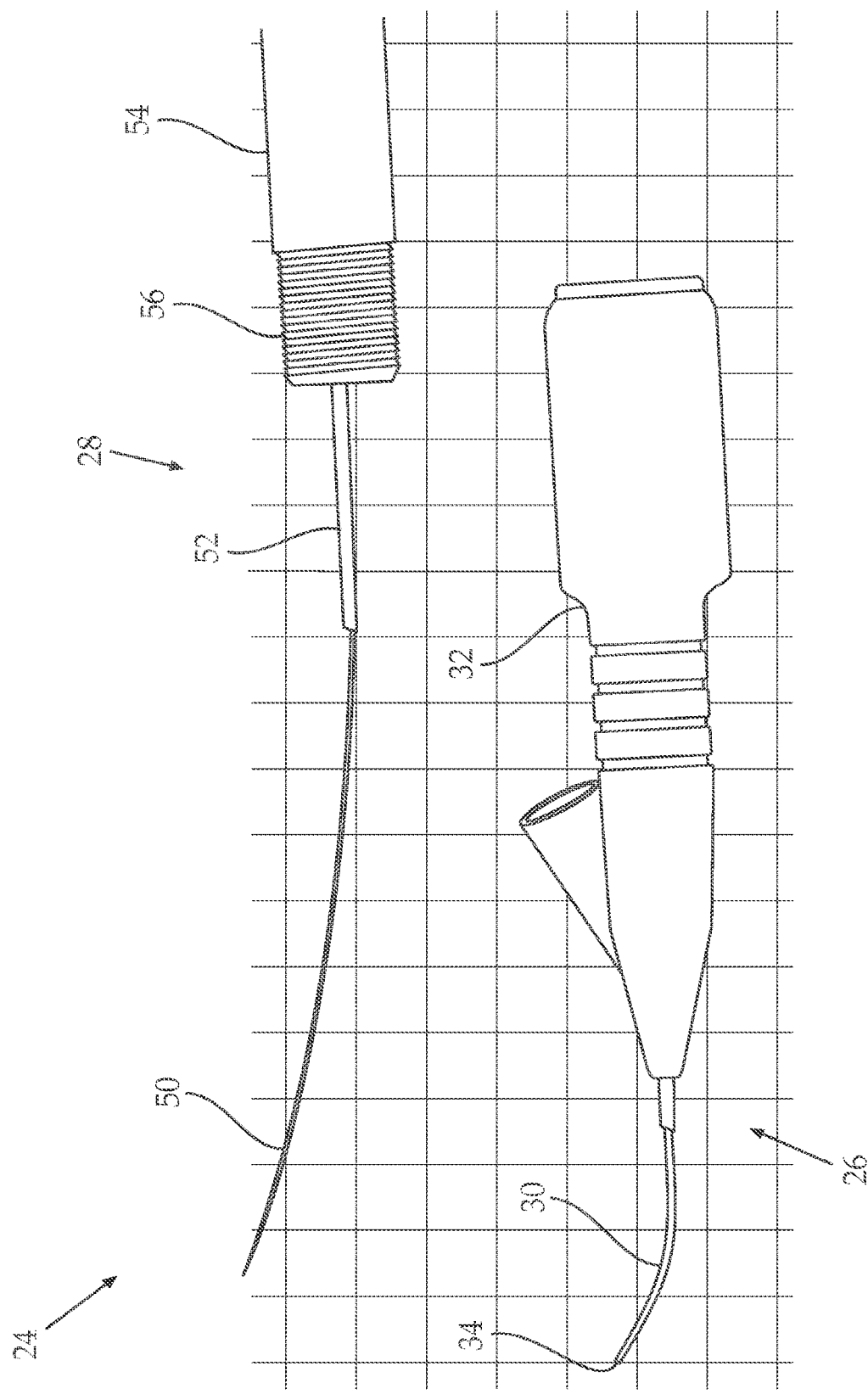

As seen in FIGS. 2A and 2B, body assembly 26 includes two main components, a needle 30 and a body 32. Each of the background blocks in FIG. 2A is 5 mm×5 mm.

Needle 30 is an upwardly curved hollow needle of surgical stainless steel having a blunt needle tip 34 at a distal end and a needle bore 36. Both needle 30 and a needle bore 36 thereof have an oval cross section (perhaps more accurately, a rounded-vertice rectangle cross section). Needle 30 has outer dimensions of 100 micrometers (height dimension) and 400 micrometers (width dimension).

Body 32 is a monolithic piece of suitable polymer (e.g., polytetrafluorethylene). As seen in FIG. 2B, body 32 is hollow having a separator assembly-accepting void 38 in fluid communication with needle bore 36 through separator passage 40 and an injector assembly-accepting void 42 in fluid communication with needle bore 36 through composition passage 44. Both separator assembly-accepting void 38 and injector assembly-accepting void 42 are provided with internal screw threads 48. Injector assembly-accepting void 42 constitutes an injection port of device 24.

As seen in FIG. 2A, separator assembly 28 includes three main components: separator 50, sealing sleeve 52 and separator assembly body 54.

Separator 50 is a thin elongated blunt-tipped wire that is a laterally flexible, axially rigid (longitudinally non-compressible) wire of surgical stainless steel having an outer diameter of 25 micrometers, and is substantially smaller than needle bore 36, inter alia, because of the shape of the cross section of needle bore 36. Specifically, the size of needle bore 36 relative to the size of the cross section of separator 50 is such that a fluid composition can flow therethrough when separator 50 is disposed therein. As noted above, in some embodiments, a separator having a larger diameter is preferred.

Sealing sleeve 52 is a tube of suitable polymer (e.g., PEEK) tightly encircling and holding separator 50 in place. The outer diameter of sealing sleeve 52 is dimensioned to sealingly slide in separator passage 40.

Separator assembly body 54 is a monolithic piece of suitable polymer (e.g., polytetrafluorethylene) having a bore into which sealing sleeve 52 and separator 50 are tightly fitted. Separator assembly body 54 is dimensioned to sealingly slide in separator assembly-accepting void 38. Separator assembly body 54 is provided with external screw threads 56 configured to engage the internal screw threads 48 of separator assembly-accepting void 38.

In FIG. 2C, body assembly 26 is depicted viewed facing blunt distal needle tip 34 when associated with separator assembly 28. Specifically, as seen with reference to FIGS. 2A and 2B separator assembly body 54 is located in separator assembly-accepting void 38, screw threads 56 engage screw threads 48 of separator assembly-accepting void 38, sealing sleeve 52 is sealingly located in separator passage 40, and separator 50 is located inside needle bore 36, but in FIG. 2C, the distal tip of separator 50 does not protrude from distal end 34 of needle 30.

Body assembly 26 and separator assembly 28 are together configured to controllably move separator 50 inside bore 36 of needle 30, allowing the distal tip of separator 50 to be controllably extended to a state where the distal tip protrudes from distal tip 34 of needle 30 by rotation of separator assembly body 54 relative to body assembly 26 in a first direction, and to be controllably retracted back into bore 36 by rotation of separator assembly body 54 relative to body assembly 26 in a direction opposite to the first. Screw threads 48 of separator assembly-accepting void 38 are such that the distal tip of separator 50 may protrude by up to but not more than 4 mm from distal tip 34 of needle 30.

Figure 2D:
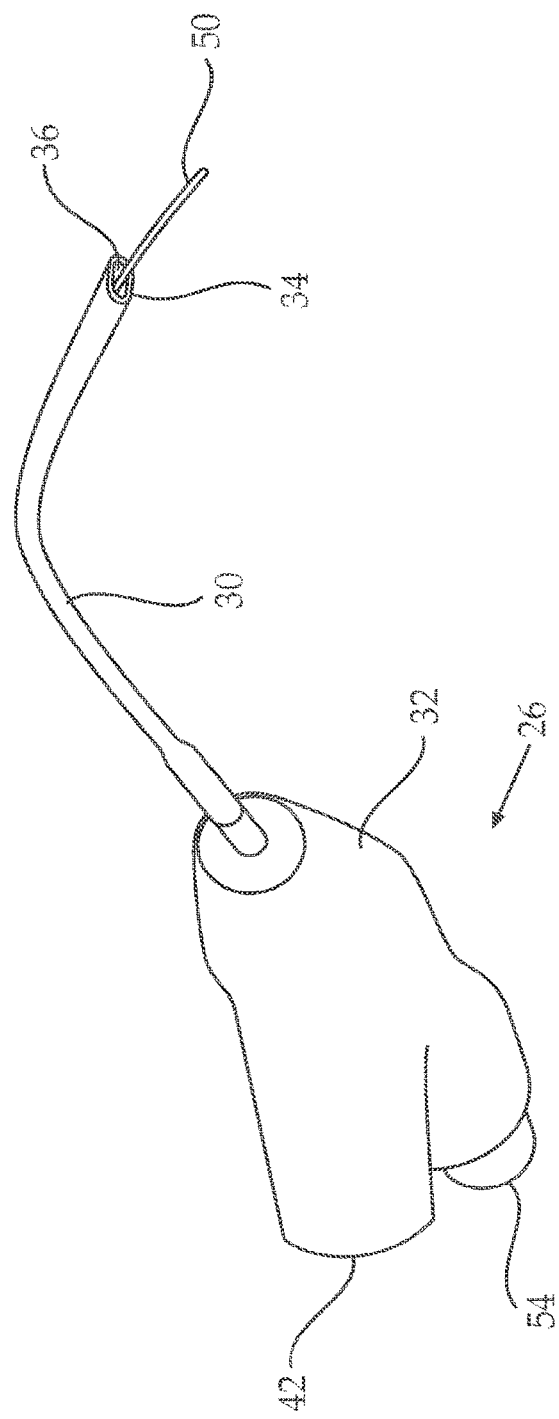

In FIG. 2D, body assembly 26 is depicted viewed facing blunt distal needle tip 34 when associated with separator assembly 28, where the distal tip of separator 50 protrudes from distal tip 34 of needle 30.

Figure 2E:
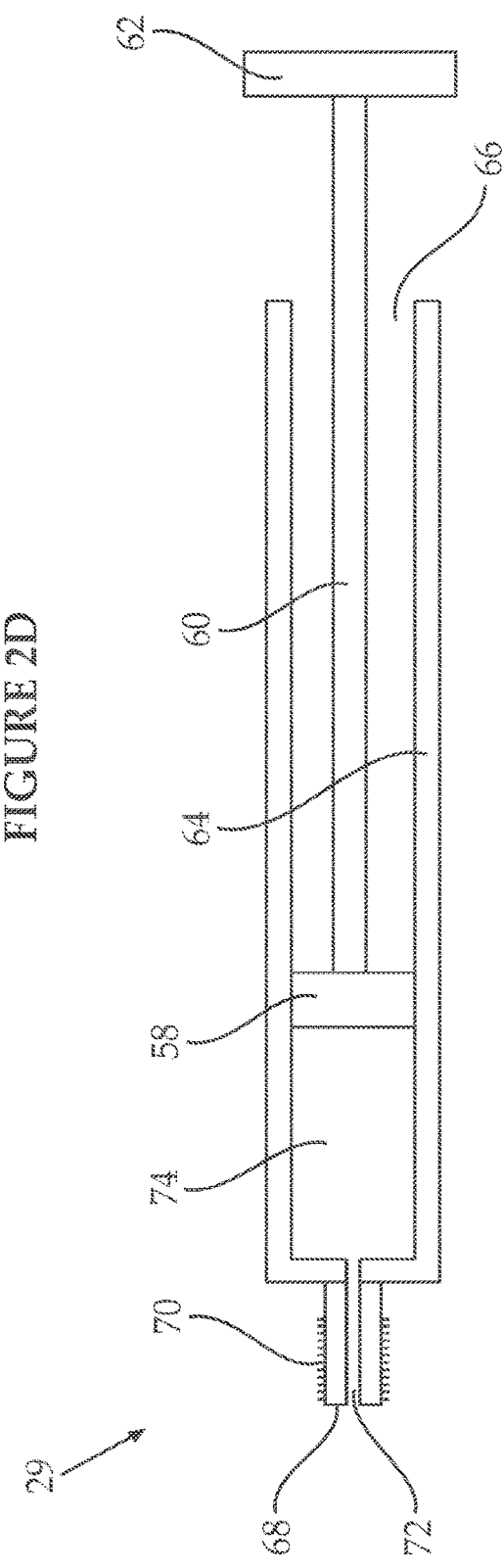

In FIG. 2E, Injector assembly 29 is substantially a syringe as known in the art and comprises: a plunger 58 mounted on the distal end of a rod 60 with an enlarged proximal end 62 and a hollow barrel 64 having a cylindrical barrel bore 66 open at a proximal end, and a smaller-dimensions adapter 68 having external screw threads 70 through which passes a composition outlet 72 in fluid communication with barrel bore 66. Plunger 58 is configured to sealingly slide inside barrel bore 66 from the proximal end, defining a composition chamber 74 which only exit is through composition outlet 72. adapter 68 is dimensioned to sealingly slidingly engage separator assembly-accepting void 38.

External screw threads 70 of adapter 68 are configured to engage the internal screw threads 48 of injector assembly-accepting void 42. When fully screwed together so that the distal end of adapter 68 contacts the distal face of injector assembly-accepting void 42, adapter 68 is sealingly secured in injector assembly-accepting void 42 and there is fluid communication between composition chamber 74 and composition passage 44 through composition outlet 72.

Figure 2F:
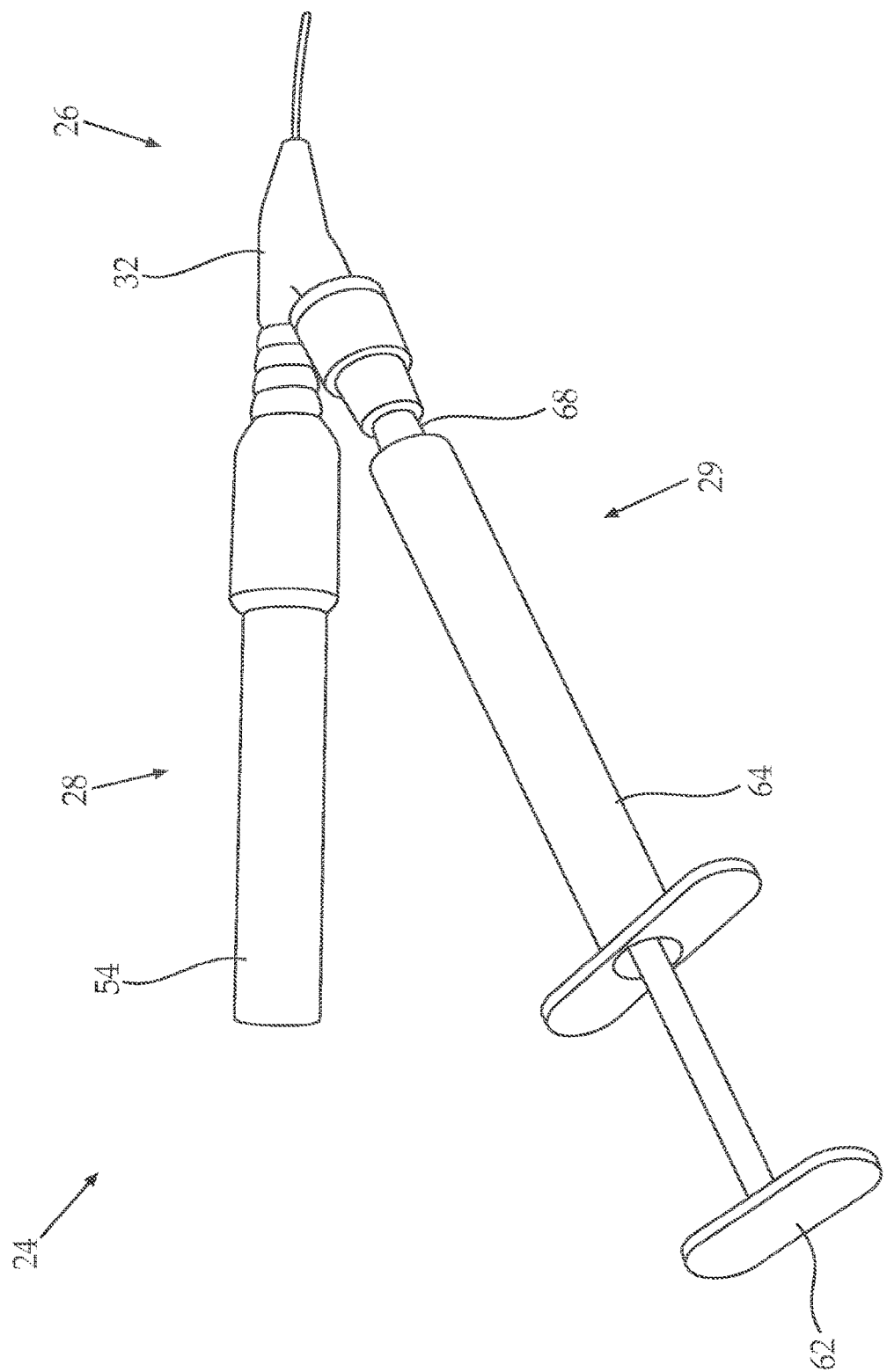

In FIG. 2F, body assembly 26 is depicted when associated with separator assembly 28 as described above, and also associated with injector assembly 29. Specifically, screw threads 70 of adapter 68 of injector assembly 29 engage screw threads 48 of injector assembly-accepting void 42 so that there is fluid communication between composition chamber 74 and composition passage 44 through composition outlet 72, into the proximal end of needle 30, through bore 36 and out distal tip 34 of needle 30.

Embodiment of a Method

An exemplary embodiment of the method according to the teachings herein implemented using the device of FIG. 2 is described hereinbelow as performed by a surgeon, with reference to FIGS. 3A-3I.

An eye 76 of a human subject is prepared in the usual way, for example by treatment with an antiseptic such as povidone-iodine.

Figure 3B:
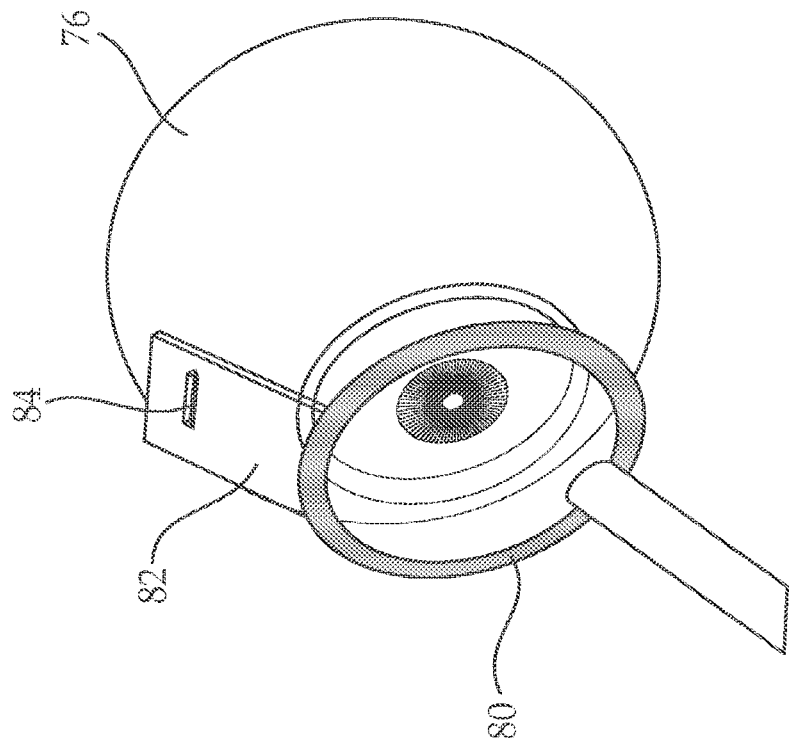
FIGS. 3A to 3I schematically depict an embodiment of a method of delivery of a fluid composition to the choroid according to the teachings herein.
Figure 3A:
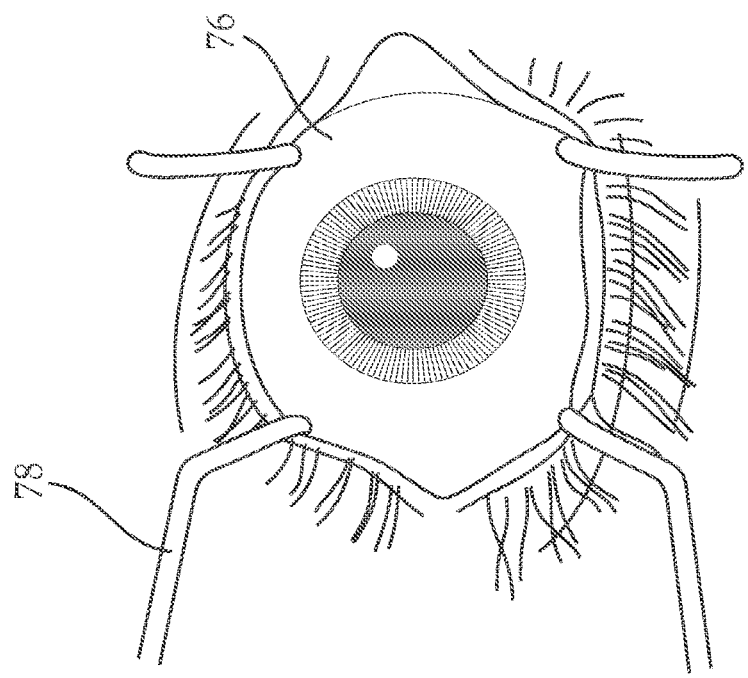

A speculum 78 is placed on eye 76 to keep the eyelids open and expose the anterior portion of eye 76, FIG. 3A As known in the art of laser eye surgery, a ring-shaped immobilization plate 80 is placed on eye 76 around the cornea and suction applied in the usual way. Eye 76 is immobilized and held firmly in place. Secured to immobilization plate 80 is a guide 82. Guide 82 includes an angled slot 84 that indicates where and at what angle a channel is to be made through the sclera.

A corneal pachymeter is used in the usual way to determine the thickness of the sclera in the region where the surgeon intends to make the channel as indicated by slot 84, for humans typically between 500-600 micrometers near the front of the eye. The amount that the knife (see below) is to be advanced to penetrate through the sclera without damaging the choroid is calculated from the measured thickness of the sclera and the angle determined by slot 84.

In the usual way, the surgeon cuts and peels back a portion of the conjunctiva to expose a portion of the sclera where the surgeon intends to make the channel.

Figure 3C:
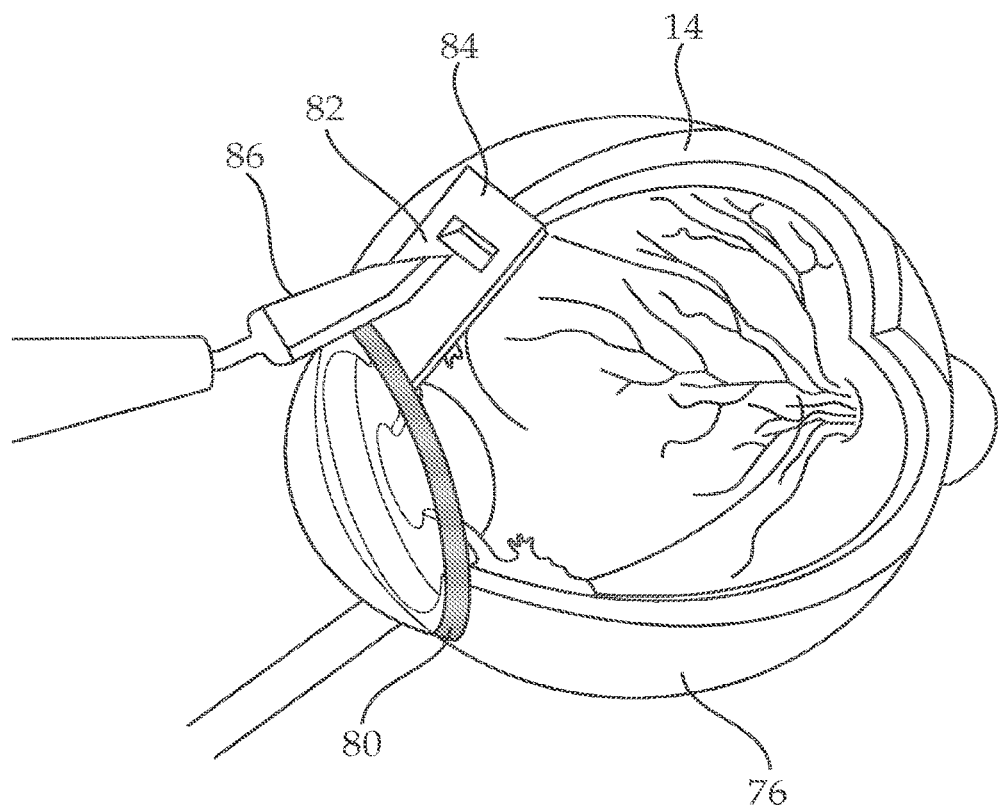

In FIG. 3C, the surgeon pushes the point of a standard tapered flat knife 86 (e.g., a diamond knife or AccuSharp® knife by Accutome Inc., Malvern, PA, USA) or as described in US 2013/0253416 by the Inventor) through slot 84 in guide 82 to pierce and then penetrate into sclera 14.

Figure 3D:
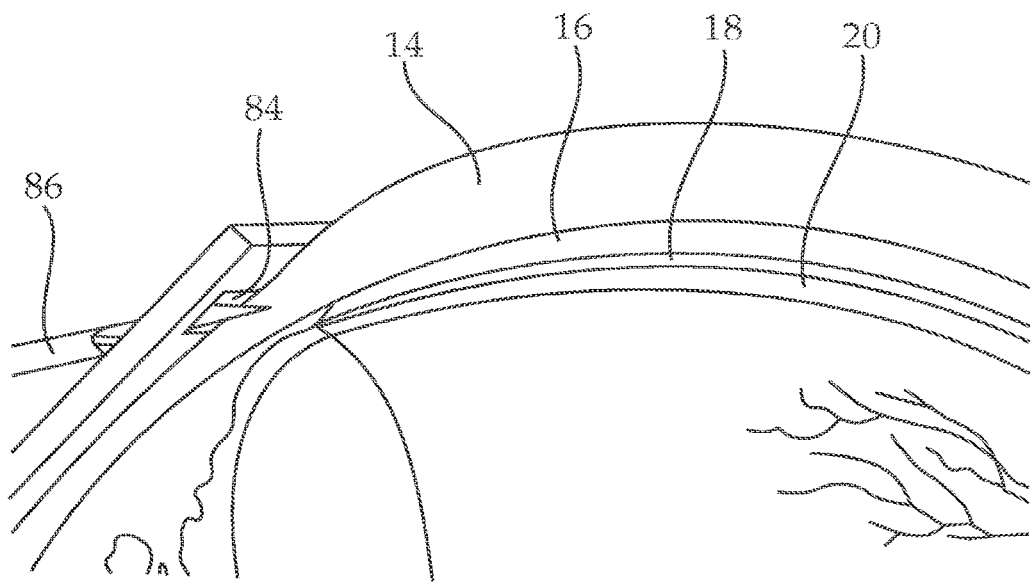

In FIG. 3D, slot 84 helps ensure that knife 86 makes a channel in sclera 14 with the desired entry point. During the penetration of knife 86, slot 84 helps maintains knife 86 at an angle not greater than 30° from parallel to the surface of the eyeball and therefore of the layers thereunder, so that the channel made is at an angle not greater than 30° from parallel to the surface of the eyeball and the layers thereunder.

Figure 3E:
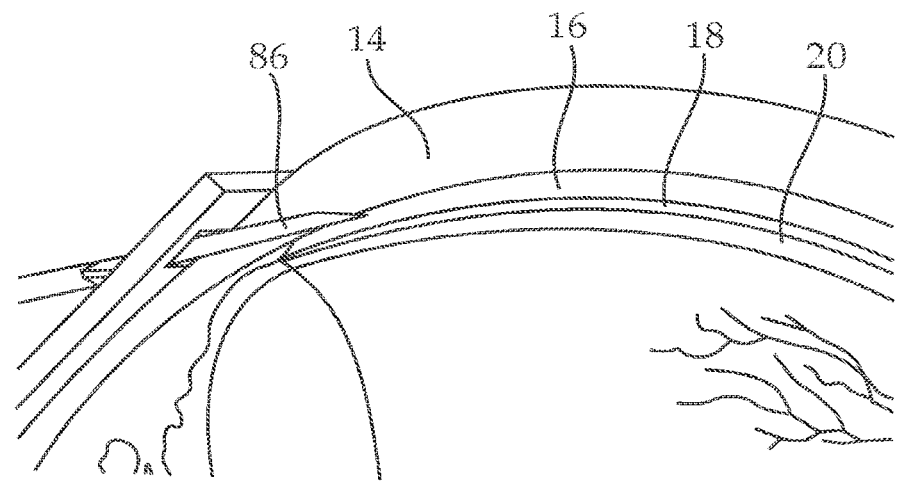

In FIG. 3E, knife 86 penetrates through sclera 14 so that the tip of knife 86 just enters choroid 16. Knife 86 is not advanced further to avoid damaging choroid blood vessels that would lead to bleeding.

Figure 3F:
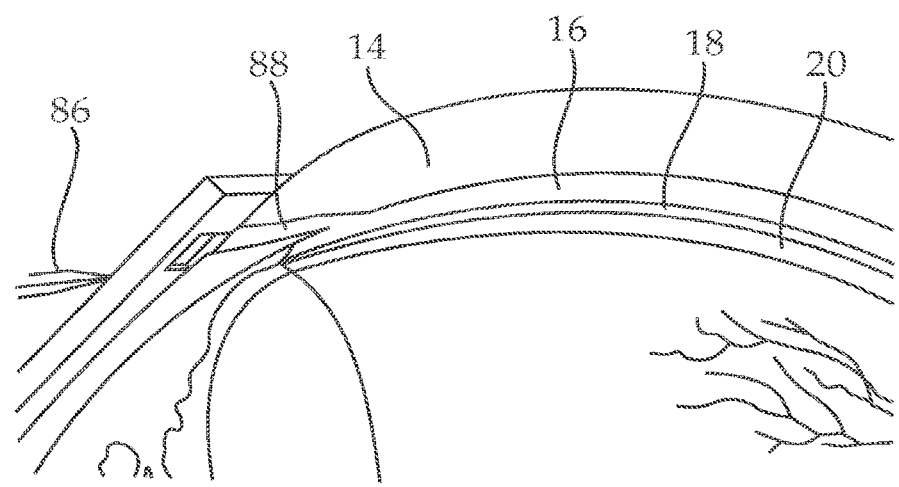

In FIG. 3F, knife 86 is withdrawn leaving a channel 88. Since knife 86 is tapered, channel 88 is a converging channel, where the dimensions of a proximal end of channel 88 near the outer portion of sclera 14 are greater than the dimensions of a distal end of the channel 88 near the inner portion of the sclera 14. Since knife 86 is flat, channel 88 is substantially a slit.

A device such as device 24 described with reference to FIG. 2 is assembled and prepared for use as described above.

Plunger 58 of injector assembly 29 is associated with barrel 64 to define a composition chamber 74. Composition chamber 74 is charged, in the usual way, with the desired fluid composition, typically a liquid therapeutic composition including an active pharmaceutical ingredient and/or viable cells. Injector assembly 29 is associated with body assembly 26 by engaging external screw threads 70 of adapter 68 with internal screw threads 48 of injector assembly-accepting void 42, to be fully screwed together so that the distal end of adapter 68 contacts the distal face of injector assembly-accepting void 42 so that that there is fluid communication between composition chamber 74 and composition passage 44 through composition outlet 72.

External screw threads of separator assembly body 54 are just engaged with the internal screw threads 48 of separator assembly-accepting void 38. In such a state, separator 50 passes through needle bore 36, where the tip of separator 50 is close to, but does not emerge from, needle tip 34 and sealing sleeve 52 sealingly passes through separator passage 40.

Figure 3G:
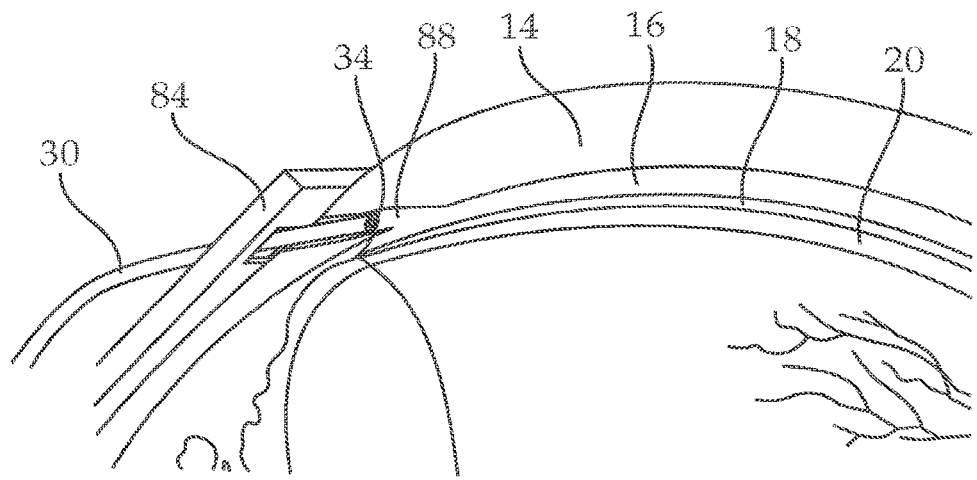

In FIG. 3G, needle tip 34 is placed through slot 84, enters channel 88 and is advanced through channel 88 so that needle bore 36 (not seen in FIG. 3G) constitutes a passage in sclera 14. The distal dimensions of channel 88 are smaller than of needle tip 34 so that advancement of needle tip 34 within channel 88 eventually stops. Needle tip 34 is pushed inwards into channel 88 in sclera 14 with sufficient force so that the tough sclera forms a seal around needle tip 34. Further, such force allows needle tip 34 to act as a tamponade to ameliorate any choroidal bleeding. The use of a blunt needle tip 34 allows a greater pressure to be applied with less chance of damage to the eye.

Subsequently, separator assembly body 54 is rotated in a direction to be drawn distally into separator assembly-accepting void 38. Consequently, separator 50 gradually emerges from needle tip 34 and advances into choroid 16, creating a separation in choroid 16, FIG. 3H.

Figure 3H:
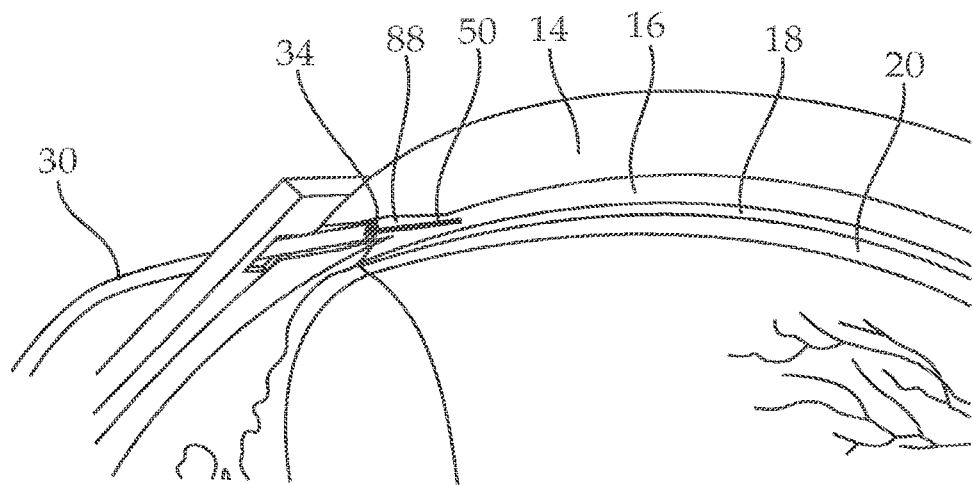
Figure 3I:
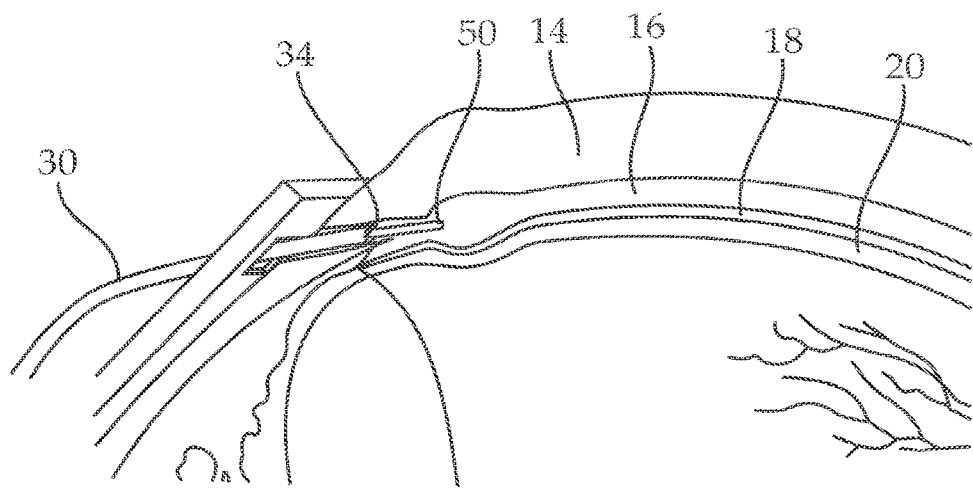

Once, in the surgeon's judgment, separator 50 has advanced sufficiently to form a sufficiently large separation in the choroid, injector assembly 29 is operated in the usual way to inject an amount of fluid composition from composition chamber 74 into the separation, FIG. 3H. The high pressure of the injected fluid that cannot be relieved by retrograde flow past the seal formed by needle tip 34 with the walls of channel 88 forces the composition to uniformly distribute in the suprachoroidal space and a portion of the extravascular matrix of choroid 16.

In some embodiments, separator 50 is at least partially retracted into needle bore 36 prior to injection of the fluid composition.

The amount of composition injected is any suitable amount. Typically, an amount of 5 microliters of fluid composition are injected when the subject is a rat and an amount of 20 to 40 microliters of fluid composition are injected when the subject is a human.

Embodiment of a Device

Figure 4:
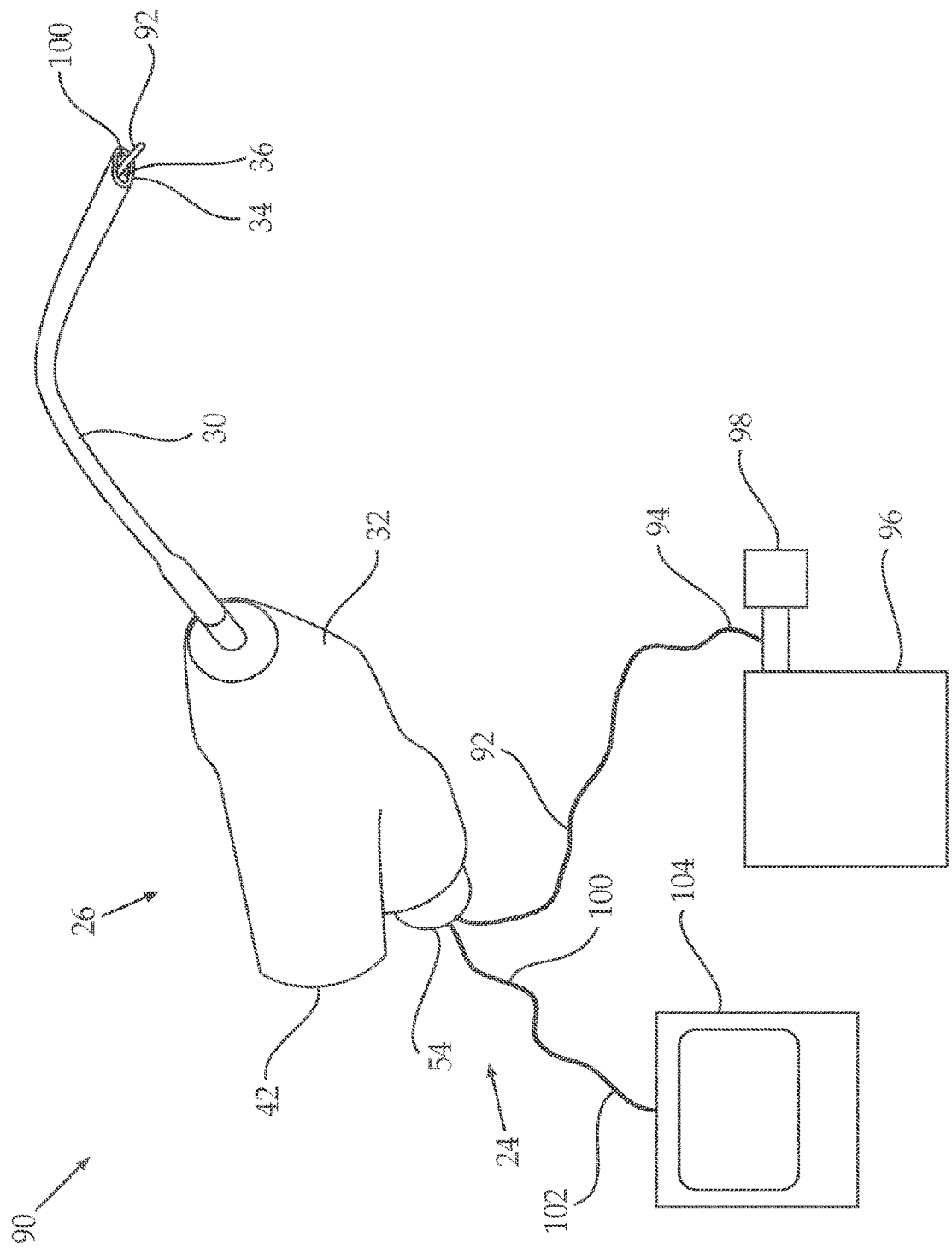
FIG. 4 is a schematic depictions of an embodiment of a device according to the teachings herein.

A device 90 according to an embodiment of the teachings herein suitable for implementing embodiments of the methods according to the teachings herein including embodiments of the methods that use light to physically damage tissue is schematically depicted viewed facing blunt distal needle tip 34 in FIG. 4. Device 90 is substantially identical to device 24 depicted in FIG. 2 and discussed herein above, with two substantial differences.

A first substantial difference is that a separator 92 of device 90 is configured to guide light suitable for physically damaging tissue from a proximal end 94 of separator 92 to the distal tip of separator 92. Proximal end 94 of separator 92 is functionally associated with a source of light suitable for physically damaging tissue, a picosecond or femtosecond laser microkeratome 96 and with a source of illumination light, a white LED 98. When LED 98 is activated, the produced white light enters separator 92 through proximal end 94 and is guided therethrough to exit through the distal tip of separator 92, illuminating whatever is located in front of the distal tip. When laser microkeratome 96 is activated, the produced light enters separator 92 through proximal end 94 and is guided therethrough to exit through the distal tip of separator 92, allowing ablation of tissue and thereby implementation of some embodiments of the teachings herein.

A second substantial difference is that device 90 further comprises an optical fiber 100 passing through bore 36 of needle 30, where the distal tip of optical fiber 100 is flush with needle tip 34. A proximal end 102 of optical fiber 100 is functionally associated with imaging component 104 (a camera and associated display screen suitable for producing an image from light gathered through the distal tip of optical fiber 100), During use of device 90, optical fiber 100 and imaging component 104 are used together to capture and display useful images. Light for capturing images is the illumination light emerging from the distal tip of separator 92.

The methods and devices described herein may be used to deliver a therapeutic composition (especially a liquid therapeutic composition) to the subretinal space of an animal (especially mammalian eye) such as a composition including a pharmaceutically effective amount of an active ingredient (e.g., an active pharmaceutical ingredient and/or a cell and/or a gene) in a suitable carrier.

The amount of therapeutic composition administered is any suitable amount and depends on factors such as the nature of the active ingredient, the concentration of the active ingredient, the treatment circumstances and the professional judgment of a treating physician and is readily calculable or determined by a person having ordinary skill in the art without undue experimentation. That said, typically the amount of composition administered to a human eye is up to about 100 microliters, up to about 75 microliters, more typically up to about 50 microliters. Typically, an amount of composition administered is between about 10 microliters and about 50 microliters.

As used herein a "therapeutic composition" refers to a preparation of one or more of the active ingredients with other components such as pharmaceutically-acceptable carriers and excipients. The purpose of a therapeutic composition is to facilitate administration of an active ingredient to a subject.

The term "pharmaceutically acceptable carrier" refers to a carrier or a diluent that does not cause significant irritation to a subject and does not substantially abrogate the activity and properties of the administered active ingredients. An adjuvant is included under these phrases. The term "excipient" refers to an inert substance added to a therapeutic composition to further facilitate administration of an active ingredient.

Therapeutic compositions used in implementing the teachings herein may be formulated using techniques with which one of average skill in the art is familiar in a conventional manner using one or more pharmaceutically-acceptable carriers comprising excipients and adjuvants, which facilitate processing of the active ingredients into a pharmaceutical composition and generally includes mixing an amount of the active ingredients with the other components. Suitable techniques are described in "Remington's Pharmaceutical Sciences," Mack Publishing Co., Easton, PA, latest edition, which is incorporated herein by reference. For example, pharmaceutical compositions useful in implementing the teachings herein may be manufactured by one or more processes that are well known in the art, e.g., mixing, blending, homogenizing, dissolving, granulating, emulsifying, encapsulating, entrapping and lyophilizing processes.

Pharmaceutical compositions suitable for implementing the teachings herein include compositions comprising active ingredients in an amount effective to achieve the intended purpose (a therapeutically effective amount). Determination of a therapeutically effective amount is well within the capability of those skilled in the art, for example, is initially estimated from animal models such as monkey or pigs.

In accordance with the above, a therapeutic composition used for implementing the teachings herein includes any suitable carrier. In some embodiments, a suitable carrier is PBS (phosphate buffered saline, e.g., 140 mM NaCl, 2.8 mM KCl, 10 mM sodium phosphate dibasic, 2 mM potassium phosphate monobasic with a pH of 7.4).

A therapeutic composition used for implementing the teachings herein includes any suitable active ingredient. In some embodiments, a therapeutic composition comprises at least one active ingredient selected from the group consisting of at least one of an active pharmaceutical ingredient, a cell and a gene.

Suitable active ingredients include, but are not limited to, active pharmaceutical ingredients such as thrombin inhibitors; antithrombogenic agents; thrombolytic agents; fibrinolytic agents; vasospasm inhibitors; calcium channel blockers; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine tri fluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; anti-proliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluorometholone, betamethasone, triamcinolone, triamcinolone acetonide); non-steroidal anti-inflammatories (such as salicylate, indomethacin, ibuprofen, diclofenac, flurbiprofen, piroxicam); antiallergenics (such as sodium chromoglycate, antazoline, methapyriline, chlorpheniramine, cetrizine, pyrilamine, prophenpyridamine); anti-proliferative agents (such as 1,3-cis retinoic acid); decongestants (such as phenylephrine, naphazoline, tetrahydrazoline); miotics and anticholinesterase (such as pilocarpine, salicylate, carbachol9 acetylcholine chloride, physostigmine, serine, diisopropyl fluorophosphate, phospholine iodine, demecarium bromide); antineoplastics (such as carmustine, cisplatin, fluorouracil); immunological drugs (such as vaccines and immune stimulants); hormonal agents (such as estrogens, estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotropin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix components; ACE inhibitors; free radical scavengers; chelators; antioxidants; anti-polymerases; photodynamic therapy agents; gene therapy agents; and other therapeutic agents such as prostaglandins, antiprostaglandins, prostaglandin precursors, proteins, peptides and the like.

In some embodiments, a therapeutic composition comprises an anti-angiogenic agent such as ranibizumab, bevacizumab, or pegaptanib, or combinations thereof.

In some embodiments, a therapeutic composition comprises an anti-vascular endothelial growth factor (anti-VEGF) agent such as macugen, lucentis, avastin, or combinations thereof.

In some embodiments, a therapeutic composition comprises a cell is selected from the group consisting of a stem cell, a forebrain-derived human cortical neural progenitor cell, a retinal progenitor cell, a mature photoreceptor cell, and an RPE cell. In some embodiments, the stem cell is selected form the group consisting of hippocampal stem cells, embryonic stem cells, bone marrow stem cells and retinal stem cells.

In some embodiments, the teachings herein are used and/or implemented for the treatment of disorders of the eye such as retinitis pigmentosa, macular degeneration (including atrophic macular degeneration), Best's disease, Stargardt's disease, Sorsby's disease, juvenile macular degeneration, central areolar choroidal dystrophy, central serous chorioretinopathy, choroidermia, choroidal melanoma, Coat's disease, cone-rod dystrophy, corneal dystrophy, Fuch's dystrophy, cystoids macular edema, diabetic retinopathy, Doyne honeycomb retinal dystrophy, hypertensive retinopathy, juvenile retinoschisis, lattice degeneration, Leber's miliarly aneurism, ocular histoplasmosis, ocular ischemic syndrome, papillophlebitis, polypoidal choroidal vasculopathy, toxoplasmosis, and Usher syndrome, vascular occlusions, inflammations such as uveitis, choroiditis and retinistis, and various tumors including neoplasms.

In some embodiments, the teachings herein are implemented to treat a disease of the eye. In some embodiments, the disease of the eye treated in accordance with the teachings herein is atrophic macular degeneration, and the therapeutic composition comprises stem cells as an active ingredient in a carrier such as PBS.

In some such embodiments, a concentration of between about 10,000 and about 60,000 cells/microliter, in some embodiments between about 20,000 and about 40,000 cells/microliter and in some embodiments between about 25,000 and about 35,000 cell s/microliter.

In some such embodiments, when the subject is human, between about 1 microliter and about 50 microliter, and in some embodiments between about 20 microliter and about 40 microliter, of therapeutic composition is administered.

Embodiments of the invention have been described herein primarily with reference to treatment of living human subjects. It is understood, however, that embodiments of the invention are performed for the veterinary or industrial (agriculture) treatment of a non-human mammal, such as pigs and other porcines, dogs and other canids, cats and other felines, horses and other equines, monkeys, apes and bovines.

Embodiments of the invention have been described herein primarily with reference to treatment of living subjects. It is understood that application of the invention for training and educational purposes (as opposed to treating a condition) falls within the scope of the claims, whether on a living non-human subject or on a dead subject, whether on a simulated human body, a human cadaver or on a non-human body, whether on a eye isolated (at least partially) from a body, or on a body.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and scope of the appended claims.

Citation or identification of any reference in this application shall not be construed as an admission that such reference is available as prior art to the invention.

Section headings are used herein to ease understanding of the specification and should not be construed as necessarily limiting.

What is claimed is:

1. A method for treatment of an eye, the method comprising:
    applying a tool to form a channel in a sclera of the eye without penetrating into a choroid of the eye, the channel tapering such that a proximal end of the channel has a cross-sectional area that is greater than a cross-sectional area that a distal end of the channel has;
    passing a distal end of a hollow needle into the channel, the needle having a bore, the distal end of the needle having a cross-sectional area that is greater than the cross-sectional area of the distal end of the channel; the distal end of the needle being constrained by the smaller cross-sectional area of the distal end of the channel from penetrating the entire thickness of the sclera.

2. The method according to claim 1, wherein said channel is sized to form a seal around said needle when said needle is located in said channel.

3. The method according to claim 1, further comprising advancing a distal tip of a separator through said bore until protruding from said distal end of said needle into the choroid, and applying said distal tip of said separator to create a separation of layers of the eye below the sclera upon physical insertion into the layers of the eye.

4. The method of claim 3, wherein the separator is laterally flexible.

5. The method of claim 3, wherein the separator is blunt-tipped or/and devoid of sharp edges.

6. The method of claim 3, wherein the separator has a cross-sectional area not more than 75% of the cross-sectional area of the bore.

7. The method of claim 3, wherein the separator is made of a material selected from the group consisting of metal, plastic, and glass.

8. The method of claim 3, wherein the separator guides light from a proximal end to the distal tip of the separator.

9. The method of claim 1, further comprising introducing an optical fiber through said channel.

10. The method of claim 9, further comprising using said optical fiber to capture images of a portion of the eye.

11. The method of claim 9, further comprising transmitting light through said optical fiber to physically damage tissue in the eye.

12. The method of claim 11, wherein the light is generated by a laser microkeratome.

13. The method of claim 1 further comprising:
    engaging an injection port with a fluid injector when the distal end of the needle is in the channel in the sclera; and
    using the fluid injector to direct a fluid through the bore of the needle.

14. The method of claim 13, further comprising advancing a distal tip of a separator through said bore until protruding from said distal end of said needle into the choroid, and applying said distal tip of said separator to create a separation of layers of the eye below the sclera upon physical insertion into the layers of the eye, wherein the fluid is directed through the bore while the separator is inside the bore.

15. The method of claim 1, further comprising advancing a distal tip of a separator through said bore until protruding from said distal end of said needle into the choroid, and applying said distal tip of said separator to create a separation of layers of the eye below the sclera upon physical insertion into the layers of the eye, wherein, for creating the separation, the separator advances into the choroid of the eye close to an interface of the sclera and the choroid.

16. The method of claim 1, wherein the tool is a knife to create a channel that is a slit.

17. A method for treatment of an eye, the method comprising:
    applying a tool to form a channel in a sclera of the eye without penetrating into a choroid of the eye, the channel tapering such that a proximal end of the channel has a cross-sectional area that is greater than a cross-sectional area that a distal end of the channel has;

passing a distal end of a hollow needle into the channel, the needle having a bore, the distal end of the needle having a cross-sectional area that is greater than the cross-sectional area of the distal end of the channel, and wherein said channel is sized to form a seal around said needle when said needle is located in said channel.

\* \* \* \* \*